United States Patent
Ogden et al.

(10) Patent No.: US 6,805,690 B2
(45) Date of Patent: Oct. 19, 2004

(54) MALE EXTERNAL CATHETERS

(75) Inventors: Jason Ogden, Santa Barbara, CA (US); John Anderson, Santa Maria, CA (US)

(73) Assignee: Mentor Corporation, Santa Barbara, CA (US)

( * ) Notice: Subject to any disclaimer, the term of this patent is extended or adjusted under 35 U.S.C. 154(b) by 90 days.

(21) Appl. No.: 10/143,521

(22) Filed: May 10, 2002

(65) Prior Publication Data

US 2003/0212375 A1 Nov. 13, 2003

(51) Int. Cl.[7] ................................................. A61F 5/44
(52) U.S. Cl. ...................................................... 604/352
(58) Field of Search ................................ 604/349, 352, 604/327, 346, 347, 351, 355; 128/844

(56) References Cited

U.S. PATENT DOCUMENTS

| | | | |
|---|---|---|---|
| 4,820,289 A | 4/1989 | Coury et al. | |
| RE33,206 E | * 5/1990 | Conway et al. | ............. 604/349 |
| 4,932,948 A | 6/1990 | Kernes et al. | |
| 5,084,037 A | 1/1992 | Barnett | |
| 5,366,449 A | 11/1994 | Gilberg | |
| 5,499,977 A | 3/1996 | Marx | |
| 5,662,631 A | 9/1997 | Marx | |
| 6,007,526 A | 12/1999 | Passalaqua et al. | |
| 6,274,154 B1 | 8/2001 | Chou | |
| 6,423,328 B2 | 7/2002 | Chou | |
| 6,551,293 B1 | * 4/2003 | Mitchell | ...................... 604/353 |
| 6,589,544 B2 | * 7/2003 | Leong | ......................... 424/402 |
| 6,699,226 B2 | * 3/2004 | Velazquez | ................... 604/349 |
| 2004/0006321 A1 | * 1/2004 | Cheng et al. | ............... 604/349 |
| 2004/0043049 A1 | * 3/2004 | Erdman | ...................... 424/402 |
| 2004/0087921 A1 | * 5/2004 | Guldfeldt | .................... 604/349 |

* cited by examiner

*Primary Examiner*—John J. Calvert
*Assistant Examiner*—Michael Bogart
(74) *Attorney, Agent, or Firm*—Fish & Richardson P.C., P.A.

(57) ABSTRACT

The invention provides male external catheters having kink-resistant drainage stems as well as methods for making male external catheters having kink-resistant drainage stems. Specifically, the invention provides male external catheters having a drainage stem designed to reduce or prevent kinking that can occur during use when a drainage hose fitting and drainage hose are attached to the catheter. The invention also provides male external catheters having skin-friendly compounds and methods for making male external catheters having skin-friendly compounds. Specifically, the invention provides male external catheters designed to have skin-friendly compounds that contact the user's skin when the catheter is being used.

6 Claims, 2 Drawing Sheets

MALE EXTERNAL CATHETERS

BACKGROUND

1. Technical Field

The invention relates to male external catheters and methods for making male external catheters.

2. Background Information

Many male patients lack the ability to control urine discharge. For example, severely injured or heavily sedated male patients can lack the muscle control needed to prevent unintended urine discharge. Men suffering from incontinence also lack the ability to control urine discharge. Thus, male patients as well as men suffering from incontinence can use male external catheters to direct discharged urine away from the body and into a collection device. Typically, male external catheters are placed over the penis in a manner similar to that of applying a condom. For example, a condom-like male external catheter can be unrolled over the penis. Once in place, the male external catheter provides a urine-impermeable barrier that directs discharged urine into a collection device protecting the user's body from urine contact.

SUMMARY

The invention features male external catheters having kink-resistant drainage stems and methods for making male external catheters having kink-resistant drainage stems. Specifically, the invention provides a male external catheter having a drainage stem with an inner diameter measuring between about seven millimeters and about eight millimeters. Such an inner diameter of the drainage stem can remain constant for no more than about 19 millimeters from the distal end toward the cylindrical member of the male external catheter. The invention also provides a male external catheter having a drainage stem with an inner diameter that is within a range measuring from about seven millimeters to about eight millimeters. Such an inner diameter can remain within that range for no more than about 19 millimeters from the distal end toward the cylindrical member. Male external catheters having these types of drainage stems can reduce or eliminate kinking when the drainage hose fitting and drainage hose are attached to the catheter. Reducing the catheter's ability to form a kink can prevent urine from leaking from the catheter. Thus, the male external catheters provided herein can be used to prevent urine leakage, eliminating the user's contact with leaked urine.

Since the materials described herein are typically elastic in nature (e.g., rubber latex or rubber silicone), it is to be understood that each measurement used herein refers to a measurement of the material in its relaxed state. Thus, the measurements used herein do not refer to measurements of materials being stretched or compressed.

The invention also features male external catheters having skin-friendly compounds and methods for making male external catheters having skin-friendly compounds. Typically, such male external catheters are configured such that the skin-friendly compounds contact the user's skin when the catheter is being used. Specifically, the invention provides a male external catheter having a cylindrical member where the inner surface of the cylindrical member contains aloe, lanolin, or a vitamin. Male external catheters having aloe, lanolin, or a vitamin can reduce or eliminate irritation or discomfort associated with wearing a male external catheter. In addition, male external catheters having aloe, lanolin, or a vitamin can help create healthy skin.

In general, the invention features a male external catheter containing a cylindrical member fluidly connected to a drainage stem having a distal end, wherein the cylindrical member is adapted to receive a penis, wherein the drainage stem has an inner diameter measuring between about seven millimeters and about eight millimeters at the distal end, and wherein the inner diameter remains constant for no more than about 19 millimeters from the distal end toward the cylindrical member. The male external catheter can contain latex, krayton, nitrile, or silicone. The cylindrical member can be capable of being rolled onto the penis. The length of the cylindrical member can be between about six centimeters and about eight centimeters. An inner surface of the cylindrical member can contain an adhesive (e.g., a medical grade pressure sensitive adhesive). An inner surface of the cylindrical member can contain aloe, lanolin, or a vitamin. An inner surface of the cylindrical member can contain an adhesive-aloe mixture. The aloe of the adhesive-aloe mixture can be from about 0.05 percent to about 5 percent of the adhesive-aloe mixture. The male external catheter can contain a bulb positioned between the cylindrical member and the drainage stem. The bulb can define an inner bulb diameter, and the cylindrical member can define an inner cylindrical member diameter, wherein the inner bulb diameter is less than the inner cylindrical member diameter and greater than the inner diameter of the drainage stem.

In another embodiment, the invention features a male external catheter containing a cylindrical member fluidly connected to a drainage stem having a distal end, wherein the cylindrical member is adapted to receive a penis, wherein the drainage stem has an inner diameter at the distal end that is within a range measuring from about seven millimeters to about eight millimeters, and wherein the inner diameter remains within the range for no more than about 19 millimeters from the distal end toward the cylindrical member. The male external catheter can contain latex, krayton, nitrile, or silicone. The cylindrical member can be capable of being rolled onto the penis. The length of the cylindrical member can be between about six centimeters and about eight centimeters. An inner surface of the cylindrical member can contain an adhesive (e.g., a medical grade pressure sensitive adhesive). An inner surface of the cylindrical member can contain aloe, lanolin, or a vitamin. An inner surface of the cylindrical member can contain an adhesive-aloe mixture. The aloe of the adhesive-aloe mixture can be from about 0.05 percent to about 5 percent of the adhesive-aloe mixture. The male external catheter can contain a bulb positioned between the cylindrical member and the drainage stem. The bulb can define an inner bulb diameter, and the cylindrical member can define an inner cylindrical member diameter, wherein the inner bulb diameter is less than the inner cylindrical member diameter and greater than the inner diameter of the drainage stem.

Another embodiment of the invention features a male external catheter containing a cylindrical member fluidly connected to a drainage stem having a distal end, wherein the cylindrical member is adapted to receive a penis, and wherein an inner surface of the cylindrical member contains aloe, lanolin, or a vitamin. The drainage stem can have an inner diameter at the distal end that measures between about seven millimeters and about eight millimeters, and the inner diameter can remain constant for no more than about 19 millimeters from the distal end toward the cylindrical member. The drainage stem can have an inner diameter at the distal end that is within a range measuring from about seven millimeters to about eight millimeters, and the inner diameter can remain within the range for no more than about 19 millimeters from the distal end toward the cylindrical member. The male external catheter can contain latex, krayton, nitrile, or silicone. The cylindrical member can be capable of being rolled onto the penis. The length of the cylindrical member can be between about six centimeters and about eight centimeters. The inner surface of the cylindrical member can contain an adhesive (e.g., a medical grade pressure sensitive adhesive). The inner surface of the cylindrical member can contain an adhesive-aloe mixture. The aloe of the adhesive-aloe mixture can be from about 0.05 percent to about 5 percent of the adhesive-aloe mixture. The male external catheter can contain a bulb positioned between the cylindrical member and the drainage stem. The bulb can define an inner bulb diameter, and the cylindrical member can define an inner cylindrical member diameter, wherein the inner bulb diameter is less than the inner cylindrical member diameter and greater than the inner diameter of the drainage stem.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

Like reference numbers and designations in the various drawings indicate like elements.

DETAILED DESCRIPTION

The invention provides male external catheters having kink-resistant drainage stems as well as methods for making male external catheters having kink-resistant drainage stems. Specifically, the invention provides male external catheters having a drainage stem designed to reduce or prevent kinking that can occur during use when a drainage hose fitting and drainage hose are attached to the catheter.

The invention also provides male external catheters having skin-friendly compounds and methods for making male external catheters having skin-friendly compounds. Specifically, the invention provides male external catheters designed to have skin-friendly compounds that contact the user's skin when the catheter is being used.

The male external catheters provided herein can be used by a male animal (e.g., a male human) to provide a kink-resistant, skin-friendly means for directing discharged urine away from the body and into a collection device. Thus, it is to be understood that each component of a male external catheter within the scope of the invention can be constructed from materials compatible with this intended use. For example, the entire male external catheter can be made from a urine-impermeable material such as rubber, latex, krayton, nitrile, or silicone. In addition, while each component of the male external catheters described herein can be made separately and then assembled to form a complete catheter, the male external catheters described herein are typically made as a single unit using common methods such as the techniques (e.g., molding techniques) used to make condoms.

Figure 1:
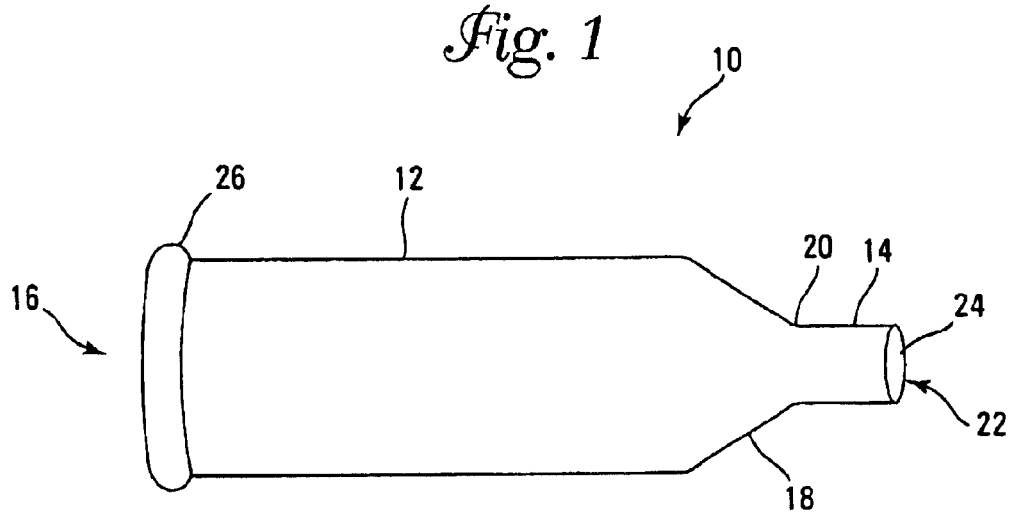
FIG. 1 is a side view diagram of a male external catheter having a kink-resistant drainage stem.

FIG. 1 is a side view diagram of a male external catheter incorporating a drainage stem that is kink-resistant. As shown in FIG. 1, male external catheter 10 can have a cylindrical member 12 fluidly connected to a drainage stem 14. The inner diameter of cylindrical member 12 can be any size capable of receiving a penis. Typically, the inner diameter of cylindrical member 12 is between about 25 millimeters and about 45 millimeters (e.g., 25, 29, 32, 36, or 41 millimeters). Cylindrical member 12 can have an open end 16 designed to receive a penis and a tapered end 18 designed to join cylindrical member 12 with drainage stem 14. The inner diameter of cylindrical member 12 from open end 16 to the beginning of the taper of tapered end 18 can be constant or variable. For example, the inner diameter of cylindrical member 12 from open end 16 to the beginning of the taper of tapered end 18 can be 25, 29, 32, 36, or 41 millimeters. Alternatively, the inner diameter of cylindrical member 12 from open end 16 to the beginning of the taper of tapered end 18 can be 25 millimeters in some places and 29 millimeters in other places. For example, the inner diameter of cylindrical member 12 can be 25 millimeters at open end 16 and 29 millimeters at the beginning of the taper of tapered end 18. Typically, the taper at tapered end 18 can be such that the inner diameter of catheter 10 at the beginning of the taper of tapered end 18 is reduced to the inner diameter of catheter 10 at drainage stem 14 over a distance between about 10 millimeters and about 14 millimeters.

As also shown in FIG. 1, drainage stem 14 can have a joining end 20 and a distal end 22. Joining end 20 can be designed to join drainage stem 14 to tapered end 18 of cylindrical member 12. Distal end 22 can be designed to define opening 24, which allows urine to exit catheter 10 when catheter 10 is being used. Opening 24 can be any size. Typically, opening 24 is the same size as the inner diameter of drainage stem 14 at distal end 22. The inner diameter of drainage stem 14 can be any size capable of allowing fluid to drain from catheter 10. In addition, the inner diameter of drainage stem 14 is typically a size sufficient to receive a drainage hose fitting. Typically, the inner diameter of drainage stem 14 is between about five millimeters and about ten millimeters (e.g., five, six, seven, eight, nine, or ten millimeters). Further, the inner diameter of drainage stem 14 can remain constant from distal end 22 toward cylindrical member 12 for a distance equal to the insertable portion of a drainage hose fitting. For example, the inner diameter of drainage stem 14 can be eight millimeters at each point from distal end 22 toward cylindrical member 12 for a distance no more than about 19 millimeters (e.g., no more than about 18, 17, 16, 15, 14, 13, 12, 11, ten, nine, eight, seven, six, five, four, or three millimeters) from distal end 22 toward cylindrical member 12. In other words, drainage stem 14 can have a length of 19 millimeters with the inner diameter of drainage stem 14 being eight millimeters over that entire 19-millimeter length.

Alternatively, drainage stem 14 can have an inner diameter at distal end 22 that is within a range measuring from about five millimeters to about ten millimeters (e.g., from about six millimeters to about nine millimeters, from about six millimeters to about eight millimeters, from about seven millimeters to about nine millimeters, or from about seven millimeters to about eight millimeters). In this case, the inner diameter of drainage stem 14 can remain within that range for no more than about 19 millimeters (e.g., no more than about 18, 17, 16, 15, 14, 13, 12, 11, ten, nine, eight, seven, six, five, four, or three millimeters) from distal end 22 toward cylindrical member 12. For example, drainage stem 14 can have a length of 19 millimeters with the inner diameter of drainage stem 14 being between seven millimeters and eight millimeters over that entire 19-millimeter length.

With further reference to FIG. 1, male external catheter 10 can be rolled and unrolled. Briefly, catheter 10 can be rolled from open end 16 toward distal end 22, producing rolled portion 26. Once rolled, catheter 10 can be unrolled in a direction toward open end 16. Rolling catheter 10 provides a convenient way for the user to apply catheter 10 over the penis, which is very similar to the way a condom is applied.

Typically, at least a portion of the inner surface of a male external catheter contains an adhesive to secure the catheter to the penis during use. For example, the entire inner surface of cylindrical member 12 can contain a coating of medical grade pressure sensitive adhesive. Such adhesives include, without limitation, silicon pressure sensitive adhesives and acrylic pressure sensitive adhesives. In addition to containing an adhesive, the male external catheters described herein can contain one or more skin-friendly compounds. Such skin-friendly compounds include, without limitation, aloe, lanolin, and vitamins (e.g., Vitamin E, Vitamin C, and/or Vitamin A). In some embodiments, the male external catheter may contain one or more adhesives. In other embodiments, the male external catheter may contain one or more skin-friendly compounds. In yet other embodiments, the male external catheter may contain one or more mixtures of adhesives and skin-friendly compounds. For example, a male external catheter may contain a mixture of medical grade pressure sensitive adhesive and aloe. The aloe in such a mixture can be in any amount. For example, from about 0.05 percent to about 5 percent (e.g., less than 5, 4, 3, 2, 1, or 0.5 percent) of an adhesive-aloe mixture can be aloe. Any form of aloe can be used including, without limitation, dry forms. When using dry aloe compounds, the dry aloe can be added to other ingredients (e.g., water, alcohols, and oils) at any ratio (e.g., 1/10, 1/100, 1/200, or 1/500).

Any method can be used to apply an adhesive and/or skin-friendly compound to a catheter. For example, adhesive and/or skin-friendly compounds can be applied to a male external catheter as the catheter is being rolled prior to packaging. Alternatively, adhesives and/or skin-friendly compounds can be added using a dipping process. For example, the surface of a male external catheter to be coated can be dipped into a mixture of adhesive and aloe. Any amount of adhesive and/or skin-friendly compound can be applied. For example, a thin coating of an adhesive-aloe mixture can be applied to the inner surface of cylindrical member 12.

Figure 2:
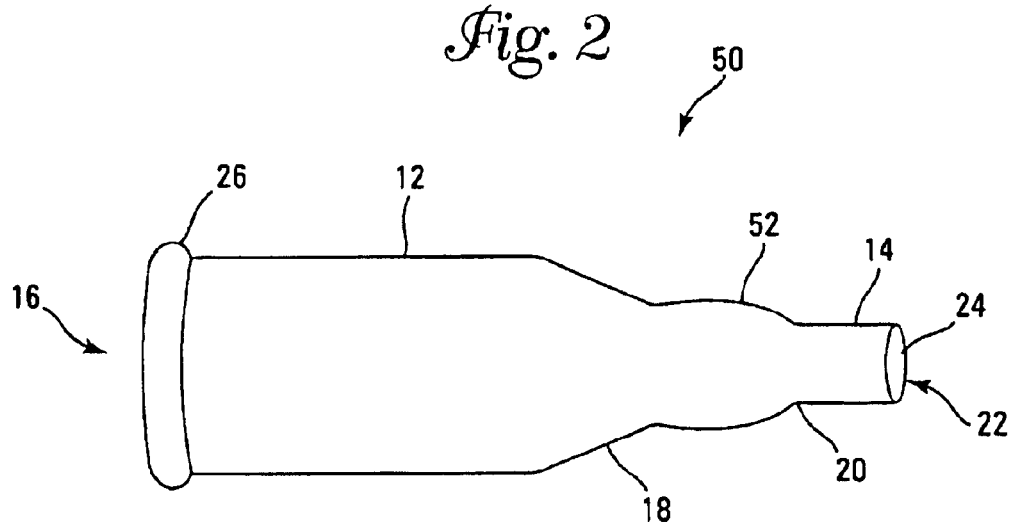
FIG. 2 is a side view diagram of a male external catheter having a bulb and a kink-resistant drainage stem.

FIG. 2 is a side view diagram of another embodiment of a male external catheter incorporating a drainage stem that is kink-resistant. As shown in FIG. 2, male external catheter 50 can have cylindrical member 12 fluidly connected to a bulb 52, which is fluidly connected to drainage stem 14. In this case, tapered end 18 can be designed to join cylindrical member 12 with bulb 52, and joining end 20 can be designed to join drainage stem 14 to bulb 52. In addition, the taper at tapered end 18 can be such that the inner diameter of catheter 10 at the beginning of the taper of tapered end 18 is reduced to the inner diameter of catheter 10 at bulb 52 over a distance between about ten millimeters and about 14 millimeters.

The inner diameter of bulb 52 can be variable. For example, as shown in FIG. 2, the inner diameter of bulb 52 can increase and then decrease along catheter 10 from tapered end 18 toward joining end 20. Typically, the minimum inner diameter within bulb 52 is between about five millimeters and about 20 millimeters (e.g., five, six, seven eight, nine, ten, 11, 12, 13, 14, 15, 16, 17, 18, 19, or 20 millimeters). The maximum inner diameter within bulb 52 is between about five millimeters and about 20 millimeters (e.g., five, six, seven eight, nine, ten, 11, 12, 13, 14, 15, 16, 17, 18, 19, or 20 millimeters).

In addition, the inner diameters within bulb 52 can be less than the inner diameter of cylindrical member 12 at open end 16 and greater than the inner diameter of drainage stem 14 at distal end 22.

Figure 3:
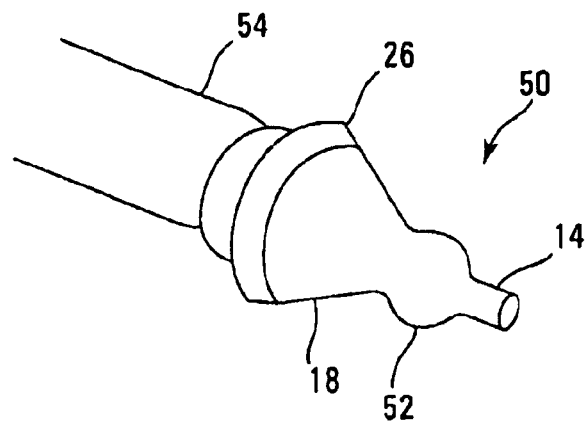
FIG. 3 is a side view diagram of the male external catheter shown in FIG. 2 being applied to a penis.

FIG. 3 is a side view diagram of male external catheter 50 partially placed over a penis. As shown in FIG. 3, male external catheter 50 can be rolled up such that most of cylindrical member 12 is within rolled portion 26. In this case, a portion of tapered end 18 is not rolled. To apply a male external catheter, catheter 50 can be placed onto penis 54 as shown in FIG. 3. Once in place, rolled portion 26 can be unrolled over the length of penis 54 in a manner similar to the way a condom is applied.

Figure 4:
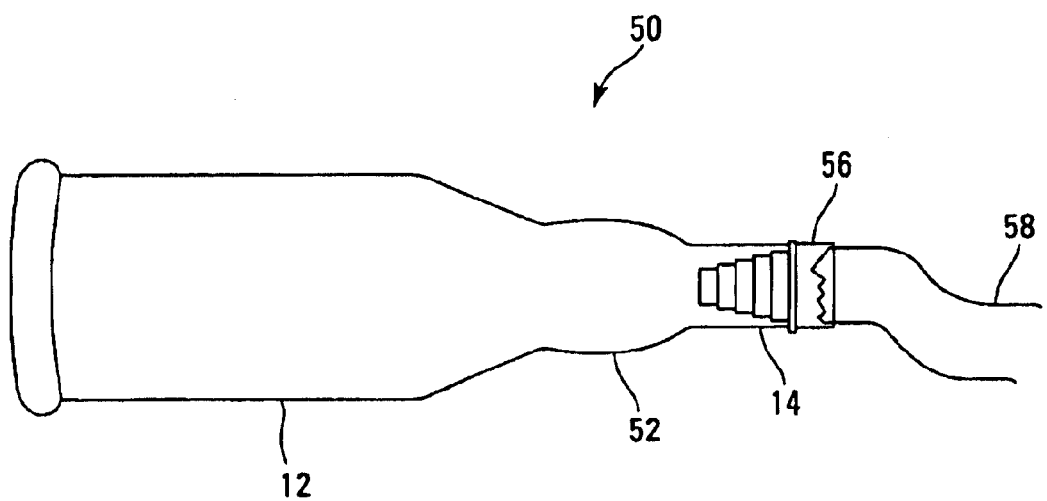
FIG. 4 is a side view diagram of the male external catheter shown in FIG. 2 attached to a drainage hose fitting and drainage hose.

FIG. 4 is a side view diagram of male external catheter 50 connected to a drainage hose fitting 56 and a drainage hose 58. Once a male external catheter is applied to a penis, drainage hose fitting 56 pre-attached to drainage hose 58 can be inserted into drainage stem 14 through opening 24 at distal end 22. Typically, the length of drainage stem 14 will be such that the insertable portion of drainage hose fitting 56 fills most, if not all, the space within drainage stem 14 without extending into the space of bulb 52.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A male external catheter comprising a cylindrical member fluidly connected to a drainage stem having a distal end, wherein said cylindrical member is adapted to receive a penis, wherein said drainage stem has an inner diameter measuring between about seven millimeters and about eight millimeters at said distal end, wherein said inner diameter remains constant for no more than about 19 millimeters from said distal end toward said cylindrical member, and wherein an inner surface of said cylindrical member comprises an adhesive-aloe mixture.

2. The male external catheter of claim 1, wherein the aloe of said adhesive-aloe mixture is from about 0.05 percent to about 5 percent of said adhesive-aloe mixture.

3. A male external catheter comprising a cylindrical member fluidly connected to a drainage stem having a distal end, wherein said cylindrical member is adapted to receive a pens; wherein said drainage stem has an inner diameter at said distal end that is within a range measuring from about seven millimeters to about eight millimeters, wherein said inner diameter remains within said range for no more than about 19 millimeters from said distal end toward said cylindrical member, and wherein an inner surface of said cylindrical member comprises an adhesive-aloe mixture.

4. The male external catheter of claim 3, wherein the aloe of said adhesive-aloe mixture is from about 0.05 percent to about 5 percent of said adhesive-aloe mixture.

5. A male external catheter comprising a cylindrical member fluidly connected to a drainage stem having a distal end, wherein said cylindrical member is adapted to receive a penis, and wherein inner surface of said cylindrical member comprises an adhesive-aloe mixture.

6. The male external catheter of claim 5, wherein the aloe of said adhesive-aloe mixture is from about 0.05 percent to about 5 percent of said adhesive-aloe mixture.

* * * * *

UNITED STATES PATENT AND TRADEMARK OFFICE
CERTIFICATE OF CORRECTION

PATENT NO. : 6,805,690 B2
DATED : October 19, 2004
INVENTOR(S) : Jason Ogden and John Anderson It is certified that error appears in the above-identified patent and that said Letters Patent is hereby corrected as shown below:

Column 6,
Line 66, please delete "pens" and insert -- penis -- therefor;

Column 8,
Line 2, after "wherein", please insert -- an --.

Signed and Sealed this

Seventeenth Day of May, 2005

JON W. DUDAS
*Director of the United States Patent and Trademark Office*